United States Patent
Litwiller et al.

(10) Patent No.: US 11,783,451 B2
(45) Date of Patent: Oct. 10, 2023

(54) SYSTEMS AND METHODS FOR REDUCING COLORED NOISE IN MEDICAL IMAGES USING DEEP NEURAL NETWORK

(71) Applicant: GE Precision Healthcare LLC, Milwaukee, WI (US)

(72) Inventors: Daniel Litwiller, Denver, CO (US); Xinzeng Wang, Houston, TX (US); Ali Ersoz, Brookfield, WI (US); Robert Marc Lebel, Calgary (CA); Ersin Bayram, Houston, TX (US); Graeme Colin McKinnon, Hartland, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 657 days.

(21) Appl. No.: 16/806,689

(22) Filed: Mar. 2, 2020

(65) Prior Publication Data
US 2021/0272240 A1   Sep. 2, 2021

(51) Int. Cl.
*G06T 5/00*   (2006.01)
*G06T 7/00*   (2017.01)
*A61B 6/00*   (2006.01)

(52) U.S. Cl.
CPC ............ *G06T 5/002* (2013.01); *A61B 6/5258* (2013.01); *G06T 7/0012* (2013.01); *G06T 2207/10024* (2013.01); *G06T 2207/10088* (2013.01); *G06T 2207/20081* (2013.01); *G06T 2207/20182* (2013.01)

(58) Field of Classification Search
None
See application file for complete search history.

(56) References Cited

PUBLICATIONS

Islam, Mohammad Tariqul, et al. "Mixed Gaussian-impulse noise reduction from images using convolutional neural network." Signal Processing: Image Communication 68 (2018): 26-41. (Year: 2018).*

Zhang, Kai, et al. "Beyond a gaussian denoiser: Residual learning of deep cnn for image denoising." IEEE transactions on image processing 26.7 (2017): 3142-3155. (Year: 2017).*

Han, Dong-Kyoon, Kyuseok Kim, and Youngjin Lee. "Development and application of a deep convolutional neural network noise reduction algorithm for diffusion-weighted magnetic resonance imaging." Journal of Magnetics 24.2 (2019): 223-229. (Year: 2019).*

Maximov, Ivan I., et al. "Spatially variable Rician noise in magnetic resonance imaging." Medical image analysis 16.2 (2012): 536-548. (Year: 2012).*

Jiang, Dongsheng, et al. "Denoising of 3D magnetic resonance images with multi-channel residual learning of convolutional neural network." Japanese journal of radiology 36.9 (2018): 566-574. (Year: 2018).*

Ichinoseki, Y. et al., "Noise Power Spectrum in Propeller MR Imaging," Magnetic Resonance in Medical Sciences, vol. 14, No. 3, Jun. 1, 2015, Available Online Mar. 31, 2015, 8 pages.

\* cited by examiner

*Primary Examiner* — Samah A Beg

(57) ABSTRACT

Methods and systems are provided for de-noising medical images using deep neural networks. In one embodiment, a method comprises receiving a medical image acquired by an imaging system, wherein the medical image comprises colored noise; mapping the medical image to a de-noised medical image using a trained convolutional neural network (CNN); and displaying the de-noised medical image via a display device. The deep neural network may thereby reduce colored noise in the acquired noisy medical image, increasing a clarity and diagnostic quality of the image.

16 Claims, 10 Drawing Sheets

SYSTEMS AND METHODS FOR REDUCING COLORED NOISE IN MEDICAL IMAGES USING DEEP NEURAL NETWORK

TECHNICAL FIELD

Embodiments of the subject matter disclosed herein relate to processing medical images, such as magnetic resonance images (MRI), (CT) images, etc., and more particularly, to reducing noise in medical images using deep neural networks.

BACKGROUND

Medical imaging systems are often used to obtain anatomical and/or internal physiological information of a subject, such as a patient. For example, a medical imaging system may be used to obtain medical images of the bone structure, the brain, the heart, the lungs, and various other features of a patient. A medical image may be an image generated by a medical imaging system. Medical imaging systems may include magnetic resonance imaging (MRI) systems, computed tomography (CT) systems, x-ray systems, ultrasound systems, and various other imaging modalities.

Medical images obtained by certain imaging modalities, such as MRI, may include one or more types of noise, which may decrease image clarity and resolution. The presence of noise in a medical image may impact diagnostic quality. In particular, k-space sampling patterns, image reconstruction, and post-processing may produce medical images with colored noise (e.g., noise that is not uniformly distributed in a spatial frequency domain) in magnetic resonance (MR) images, which may be difficult to reduce with existing image processing methods. Deep learning approaches have been proposed for use in removing colored noise from medical images, however the performance of current deep learning approaches in removing colored noise is inconsistent, and often does not produce a sufficient degree of noise reduction. Therefore, exploring deep learning techniques to identify new ways for consistently reduce colored noise in medical images is generally desired.

SUMMARY

The present disclosure at least partially addresses the issues described above. In one embodiment, the present disclosure provides a method, comprising: acquiring a medical image via an imaging system, wherein the medical image comprises colored noise, mapping the medical image to a de-noised medical image using a trained convolutional neural network (CNN), and displaying the de-noised medical image via a display device. By mapping the medical image comprising colored noise to a de-noised medical image using the trained CNN, colored noise in the image may be significantly reduced, thereby increasing the clarity and diagnostic quality of the image.

The above advantages and other advantages and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
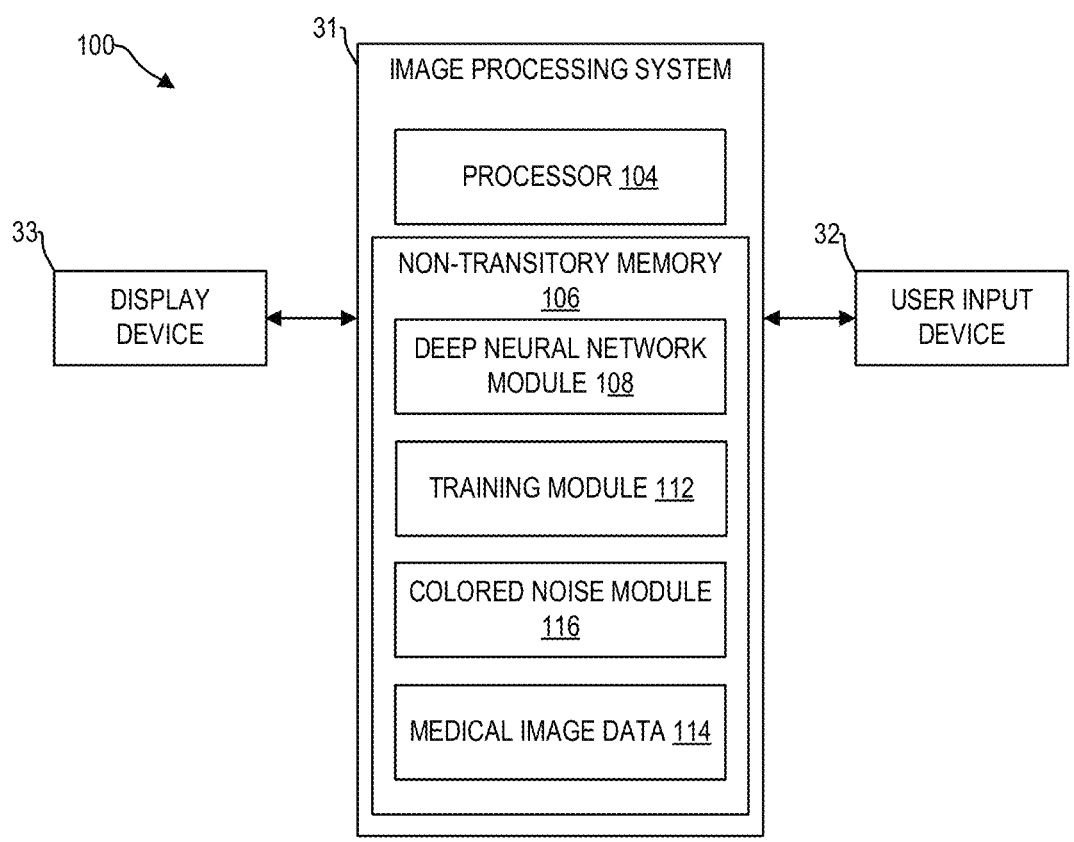
FIG. 1 is a schematic diagram illustrating an image processing system for removing colored noise from medical images using a deep neural network, according to an exemplary embodiment.

The drawings illustrate specific aspects of the described systems and methods for reducing colored noise in a medical image using a deep neural network. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

In magnetic resonance imaging (MRI), a subject is placed in a magnet. A subject is a human (live or deceased), an animal (live or deceased), or part of a human or an animal. When the subject is in the magnetic field generated by the magnet, magnetic moments of nuclei, such as protons, attempt to align with the magnetic field but precess about the magnetic field in a random order at the nuclei's Larmor frequency. The magnetic field of the magnet is referred to as B0 and extends in the longitudinal or z direction. In acquiring an MRI image, a magnetic field (referred to as an excitation field B1), which is in the x-y plane and near the Larmor frequency, is generated by a radio-frequency (RF) coil and may be used to rotate, or "tip," the net magnetic moment Mz of the nuclei from the z direction to the transverse or x-y plane. A signal, which is referred to as an MR signal, is emitted by the nuclei, after the excitation signal B1 is terminated. To use the MR signals to generate an image of a subject, magnetic field gradient pulses (Gx, Gy, and Gz) are used. The gradient pulses are used to scan through the k-space, the space of spatial frequencies or inverse of distances. A Fourier relationship exists between the acquired MR signals and an image of the subject, and therefore the image of the subject can be derived by reconstructing the MR signals. As used herein, frquency refers specifically to a spatial frequency, rather than to a temporal frequency domain.

Medical images may include noise, which limits image resolution and degrades diagnostic quality. In one example, magnetic resonance (MR) images may include white noise due to thermal energy provided by a patient during the imaging process. White noise is uniformly distributed in a spatial frequency domain (e.g., k-space) of the image. The acquired radio frequency MR data typically contain uniform noise, and if this data is used to fill k-space in a uniform manner, then the noise in k-space is uniform (e.g., white noise). However, certain image acquisition and image processing procedures may produce colored noise in medical images. Colored noise is not uniformly distributed in the k-space of the image, and may be more difficult to reduce using existing methods. As an example, colored noise in magnetic resonance (MR) images may result from non-uniform over-sampling, with some sampling overlapping with and or exceeding a Nyquist sampling criterion in at least one region of the frequency domain. As another example, colored noise in MR images may result from non-uniform under-sampling due to noise amplification during image reconstruction, such as during a kernel-based parallel imaging reconstruction. As yet another example, colored noise in MR images may result from a variable receive bandwidth or a variable readout velocity. As still another example, colored noise in MR images may result from image post-processing techniques, such as image smoothing, image sharpening, and so on. As yet another example, noise coloration may result from combining multiple images (or multiple k-space image representations). For example, multiple images may be averaged during an image post-processing technique, which may alter noise coloration. In a further example, colored noise in MR images may result from nonuniform spatial weighting, wherein different portions of the medical image may have distinct noise distribution, leading to noise coloration.

The process of removing colored noise from medical images may be complicated when the type/source of noise is not known, or when multiple sources of colored noise are present. For example, an MR image may include a first type of colored noise due to a non-uniform sampling pattern such as a Periodically Rotated Overlapping Parallel Lines with Enhanced Reconstruction (PROPELLER) sampling pattern, and a second type of colored noise due to image sharpening during post-processing. Noise is inherently stochastic, and may be difficult to accurately reduce via traditional computational methods, especially without complete knowledge of the k-space sampling pattern and any other image processing performed.

The following description relates to various embodiments for removing colored noise from medical images using deep neural networks, which at least partially addresses the above identified issues. In particular, a medical image is acquired by an imaging system, and may be subject to reconstruction and post-processing. The acquired medical image, which may include colored noise, is then processed using a trained deep neural network, which may optionally be given one or more noise parameters for the image. A medical image including colored noise is herein defined as a noisy image. Noise parameters may correlate to a type and distribution of colored noise in a medical image, and may include various imaging system settings used to acquire the medical image, such as a k-space sampling pattern. Noise parameters may further include a noise power in the spatial frequency domain, and other information about the noisy image, for example. In other words, the noise parameters may correspond to a source of colored noise in the medical image. The deep neural network may reduce colored noise in the image and output an image with substantially less colored noise (e.g., a de-noised image). In this way, de-noised medical images may be produced from corresponding noisy medical images. Further, the deep neural network may be trained before being put in use. In an embodiment, training data for the neural net may be generated by synthesizing colored noise based on noise parameters, such as based on a k-space sampling pattern.

As used herein, de-noising is the process of reducing noise in medical images, such as colored noise. Noise may be synthesized in the frequency domain as a function of noise power, and may be distributed differently in the frequency domain based on characteristics of the noise. Thus, de-noising comprises a process of at least partially reducing the presence of at least one type of colored noise in an image in order to improve image resolution and diagnostic quality. De-noised images may be produced by de-noising a noisy image (e.g., a medical image with colored noise), and conversely, noisy images may be produced by introducing one or more sources of colored noise into a pristine image (e.g., a medical image without colored noise). In particular, a noisy image may be produced from a corresponding pristine image based on a k-space sampling pattern and/or expected noise characteristics, and the resulting image pair (e.g., the noisy image and the corresponding pristine image) may be used as training data for a deep neural network. It will be appreciated that in some conditions, pristine medical images may be acquired directly using an imaging system.

Referring to FIG. 1, a medical image processing system 100 is shown, in accordance with an exemplary embodiment. In some embodiments, the medical image processing system 100 is incorporated into a medical imaging system, such as an MR system. In some embodiments, the medical image processing system 100 is disposed at a device (e.g., edge device, server, etc.) communicably coupled to the medical imaging system via wired and/or wireless connections. In some embodiments, the medical image processing system 100 is disposed at a separate device (e.g., a workstation) which can receive images from the medical imaging system or from a storage device which stores the images generated by the medical imaging system. The medical image processing system 100 may comprise image processing system 31, user input device 32, and display device 33.

Image processing system 31 includes a processor 104 configured to execute machine readable instructions stored in non-transitory memory 106. Processor 104 may be single core or multi-core, and the programs executed thereon may be configured for parallel or distributed processing. In some embodiments, the processor 104 may optionally include individual components that are distributed throughout two or more devices, which may be remotely located and/or configured for coordinated processing. In some embodiments, one or more aspects of the processor 104 may be virtualized and executed by remotely-accessible networked computing devices configured in a cloud computing configuration.

Non-transitory memory 106 may store deep neural network module 108, colored noise module 116, training module 112, and medical image data 114. Deep neural network module 108 may include one or more deep neural networks, comprising a plurality of parameters (including weights, biases, activation functions), and instructions for implementing the one or more deep neural networks to receive noisy medical images and map the noisy medical image(s) to output, wherein a de-noised medical image corresponding to the noisy medical image may be produced from the output. For example, deep neural network module 108 may store instructions for implementing a neural network, such as the convolutional neural network (CNN) of CNN architecture 300, shown in FIG. 3. However, other architectures such as combinations of fully connected networks and CNNs or generative adversarial networks and their variants can be used as well.

Deep neural network module 108 may include trained and/or untrained neural networks and may further include various data, or tags pertaining to the one or more neural networks stored therein. In some embodiments, the deep neural network tags may include an indication of the training data used to train a deep neural network, a training method employed to train the deep neural network, an accuracy/validation score of the deep neural network, and a type of anatomy/imaging protocol for which the deep neural network may be applied.

Non-transitory memory 106 further stores colored noise module 116, which comprises instructions for synthesizing colored noise based on expected k-space sampling patterns. Colored noise module 116 may include instructions that, when executed by processor 104, cause image processing system 31 to conduct one or more of the steps of method 500, discussed in more detail below. In some embodiments, colored noise module 116 includes instructions for generating a spatial representation of colored noise based on a k-space sampling patterns by weighting a k-space (e.g., spatial frequency domain) representation of white noise by the noise power derived from a sampling density map, and then transforming the resulting k-space representation to the spatial domain. The colored noise reduction module 116 may be used by training module 112 to generate training images for training the deep neural network.

Non-transitory memory 106 may further store training module 112, which comprises instructions for training one or more of the deep neural networks stored in deep neural network module 108. Training module 112 may include instructions that, when executed by processor 104, cause image processing system 31 to conduct one or more of the steps of method 700, discussed in more detail below. In some embodiments, training module 112 includes instructions for implementing one or more gradient descent algorithms, applying one or more loss functions, and/or training routines, for use in adjusting parameters of one or more deep neural networks of deep neural network module 108. In some embodiments, training module 112 includes instructions for generating training data pairs from medical image data 114. In some embodiments, training data pairs comprise corresponding pairs of noisy and pristine medical images of a same anatomical region. In some embodiments, training module 112 includes instructions for generating training data pairs by applying/adding noise synthesized by colored noise module 116 to pristine medical images to produce a noisy medical image. In some embodiments, the training module 112 is not disposed at the image processing system 31. The deep neural network module 108 includes trained and validated network(s).

Non-transitory memory 106 further stores medical image data 114. Medical image data 114 includes for example, MR images acquired using an MRI system, ultrasound images acquired by an ultrasound system, etc. For example, the medical image data 114 may store noisy and/or pristine medical images. In some embodiments, medical image data 114 may include a plurality of training data pairs comprising pairs of noisy and pristine medical images.

In some embodiments, the non-transitory memory 106 may include components disposed at two or more devices, which may be remotely located and/or configured for coordinated processing. In some embodiments, one or more aspects of the non-transitory memory 106 may include remotely-accessible networked storage devices configured in a cloud computing configuration.

Image processing system 100 may further include user input device 32. User input device 32 may comprise one or more of a touchscreen, a keyboard, a mouse, a trackpad, a motion sensing camera, or other device configured to enable a user to interact with and manipulate data within image processing system 31. As an example, user input device 32 may enable a user to make a selection of a medical image on which to perform colored noise reduction.

Display device 33 may include one or more display devices utilizing virtually any type of technology. In some embodiments, display device 33 may comprise a computer monitor, and may display unprocessed and processed MR images and/or parametric maps. Display device 33 may be combined with processor 204, non-transitory memory 206, and/or user input device 32 in a shared enclosure, or may be peripheral display devices and may comprise a monitor, touchscreen, projector, or other display device known in the art, which may enable a user to view medical images, and/or interact with various data stored in non-transitory memory 206.

It should be understood that image processing system 100 shown in FIG. 1 is for illustration, not for limitation. Another appropriate image processing system may include more, fewer, or different components.

As an example, a system comprises: a magnetic resonance imaging (MRI) system, a memory storing a trained deep neural network, a display device, and a processor communicably coupled to the memory and configured to remove colored noise from medical images.

Figure 2:
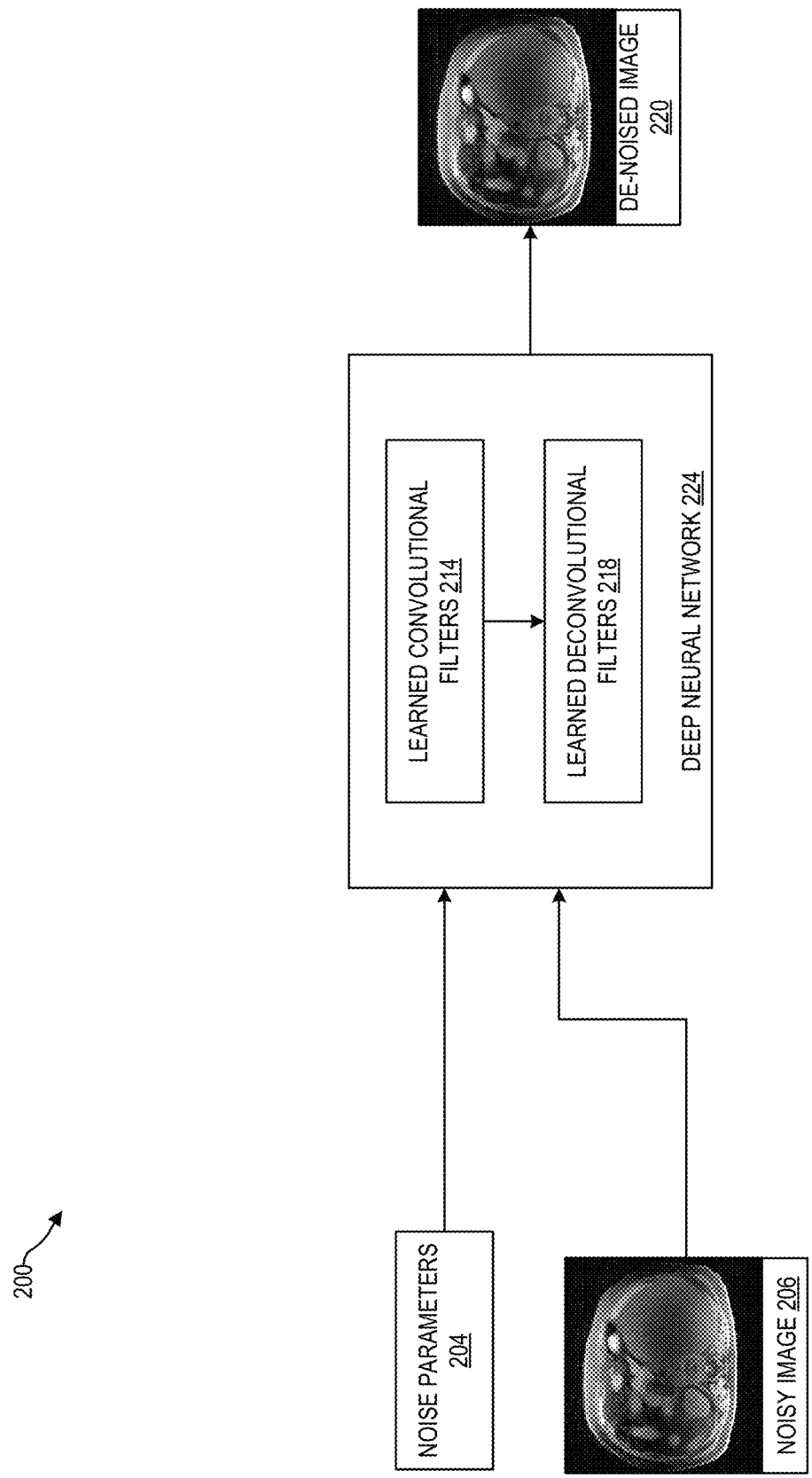
FIG. 2 is a schematic diagram illustrating the layout of an embodiment of a deep neural network, which can be used in the image processing system of FIG. 1, according to an exemplary embodiment.

Turning to FIG. 2, a schematic of a first embodiment of a colored noise reduction process 200 for reducing colored noise in a medical image is shown. Colored noise reduction process 200 may be implemented by image processing system 100 to at least partially reduce colored noise in a noisy medical image. Colored noise reduction process 200 serves to illustrate an embodiment of a noise reduction system, wherein a deep neural network 224 is used to reduce colored noise in a noisy medical image 206. In some embodiments, noise parameters 204 may be incorporated into the deep neural network 224. Noise parameters 204 may characterize the colored noise in noisy medical image 206. As an example, noise parameters 204 may include a k-space sampling pattern, a k-space sampling density, a noise density, an image processing parameter, and so on. By incorporating noise parameters 204, the deep neural network 224 may receive at least partial information regarding the extent, type, and distribution of colored noise in noisy medical image 206, in order to increase an amount and accuracy of colored noise reduction. In some embodiments, noise parameters 204 may not be incorporated into the deep neural network 224, and the deep neural network may reduce colored noise in noisy medical image 206 without information regarding noise characteristics for the image.

Colored noise reduction system 200 comprises a deep neural network 224, which receives inputs including noise parameters 204 and a noisy medical image 206, and produces a de-noised image (e.g., an imaged with reduced colored noise) as an output. Inputs are received by deep neural network 224, and mapped to de-noised image 220. Deep neural network 224 comprises learned convolutional filters 214 (learned during a training process) and learned deconvolutional filters 218 (learned during a training process). By propagating inputs through the convolutional and deconvolutional layers of deep neural network 224, de-noised image 220 is produced.

Noise parameters 204 may include one or more parameters at least partially characterizing noise in noisy medical image 206. For example, noise parameters 204 may include a k-space noise power. As another example, noise parameters 204 may include a spatial map of noise power in k-space. In some examples, noise parameters 204 may be determined based on an acquisition method, while in other examples, noise parameters 204 may be determined independently of the acquisition method. For example, noise parameters 204 may include whether a certain type of colored noise is expected based on image processing techniques applied to noisy medical image 206 before de-noising.

In an embodiment, noise parameters 204 includes acquisition data for the noisy medical image 206. The acquisition data for the medical image comprise one or more settings used by an imaging system during acquisition of noisy medical image 206, and/or one or more physiological attributes of an imaged tissue/patient and/or environmental conditions. For example, if the noisy medical image 206 is an MR image, the acquisition data may comprise one or more of an echo train length, a repetition time, an echo time, an echo spacing, a target flip angle(s), a k-space sampling pattern, a k-space sampling density, an acquisition order, a physiological signals, or other parameters/settings used by an MRI system during acquisition of noisy medical image 206, or relating to an imaged patient. Acquisition data may further include whether post-processing (e.g., such as image sharpening) has been applied to noisy medical image 206. In particular, the k-space sampling pattern and the k-space sampling density may impact the type(s) and distribution(s) of colored noise in a medical image, especially when the k-space sampling pattern is characterized by nonuniform oversampling or nonuniform undersampling. As an example, a k-space sampling pattern with nonuniform oversampling may produce noise coloration due to nonuniform noise reduction.

Noisy medical image 206 is a medical image of an anatomical region, comprising a plurality of values, wherein each value may be referred to as a pixel (for 2D images) or voxel (for 3D images). Noisy medical image 206 includes noise, which may generally be described as an unwanted visual data that degrades the quality of a medical image. Further, noise may be mathematically described as a degree of randomness in the frequency domain, wherein the color of the noise is determined by its distribution in the frequency domain. As an example, noisy medical image 206 comprises an MR image of human abdomen comprising one or more varieties of colored noise, wherein an extent and/or type of noise varies within a k-space representation of noisy medical image 206. That is, a k-space representation of noisy medical image 206 may comprise a first region having a distribution of noise, and a second region comprising a second distribution of noise, wherein the first and second distributions of noise are not the same.

Inputs, which may include noise parameters 204, may be propagated through the plurality of layers within deep neural network 224, to map intensity values of noisy medical image 206 to intensity values of de-noised image 220. As an example, deep neural network 224 may determine a set of weights to apply based on noise parameters 204. Deep neural network 224 comprises learned convolutional filters 214, and learned deconvolutional filters 218. Deep neural network 224 may further comprise one or more densely connected layers (not shown), and one or more pooling layers (not shown), one or more up sampling layers (not shown), and one or more ReLU layers (not shown), or any layers conventional in the art of machine learning. Noise parameters 204 may be incorporated into deep neural network 224 directly, by setting convolutional filters 214 and/or de-convolutional filters 218 based on noise parameters 204. In other embodiments, noise parameters 204 may each be incorporated into the deep neural network 324 via a plurality of distinct mechanisms/channels. In still other embodiments, noise parameters 204 may not be provided to deep neural network 224.

Output of deep neural network 224 may be used to produce de-noised image 220, which comprises an image of a same anatomical region as noisy medical image 206, but with colored noise at least partially reduced.

Figure 3:
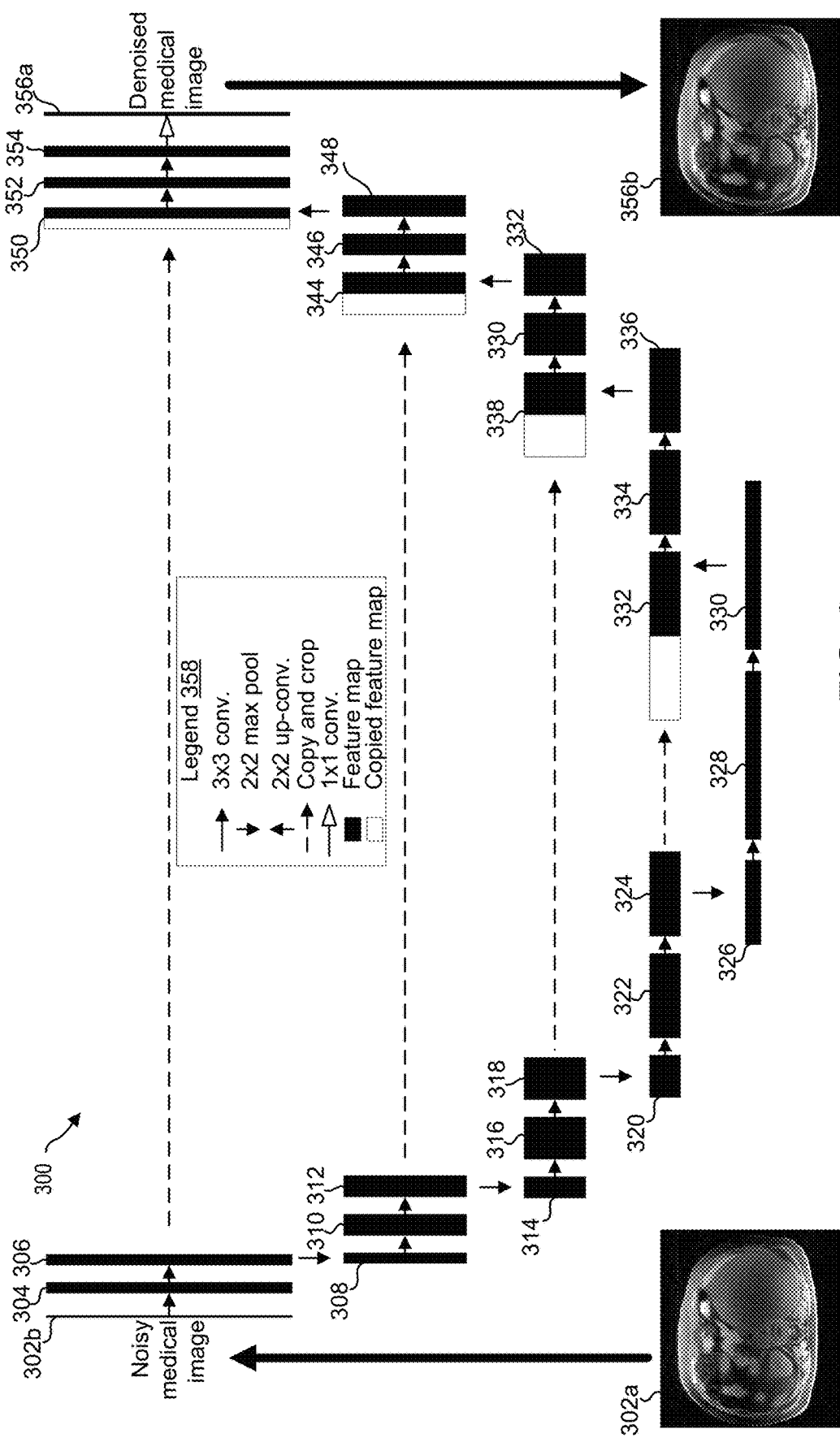
FIG. 3 is a schematic diagram illustrating an architecture of a deep neural network which can be used in the system of FIG. 1, according to an exemplary embodiment.

Turning to FIG. 3, an exemplary CNN architecture 300 for mapping a noisy medical image to a de-noised medical image is shown. CNN architecture 300 provides a more detailed illustration of a deep neural network, such as deep neural network 224, which may execute colored noise reduction of a noisy medical image. In some embodiments, a subset of the parameters of CNN architecture 300 may be selected/determined based on noise parameters. For example, as indicated in colored noise reduction system 200 shown in FIG. 2, CNN architecture 300 may incorporate one or more noise parameters.

CNN architecture 300 shown in FIG. 3 represents a U-net architecture, which may be divided into an autoencoder portion (descending portion, elements 302b-330) and an autodecoder portion (ascending portion, elements 332-356a). CNN architecture 300 is configured to receive medical images including colored noise, which may be a magnetic resonance (MR) image. In one embodiment, CNN architecture 300 is configured to receive data from a noisy medical image of an anatomical region, such as noisy medical image 302a, comprising a plurality of pixels/voxels, and map the input noisy medical image data to a de-noised medical image of the same anatomical region, such as de-noised medical image 356b. CNN architecture 300 comprises a series of mappings, from an input image tile 302b, which may be received by an input layer, through a plurality of feature maps, and finally to an output de-noised medical image 356b, which may be produced based on output from output layer 356a.

The various elements comprising CNN architecture 300 are labeled in legend 358. As indicated by legend 358, CNN architecture 300 includes a plurality of feature maps (and/or copied feature maps) connected by one or more operations (indicated by arrows). The arrows/operations receive input from either an external file, or a previous feature map, and transform/map the received input to output to produce a next feature map. Each feature map may comprise a plurality of neurons, where in some embodiments, each neuron may receive input from a subset of neurons of a previous layer/feature map, and may compute a single output based on the received inputs, wherein the output may be propagated/mapped to a subset, or all, of the neurons in a next layer/feature map.

Feature maps may be described using the terms length, width, and depth, wherein each term refers to a number of neurons comprising the feature map (e.g., how many neurons long, how many neurons wide, and how many neurons deep, a specified feature map is). Length and width, as used in reference to a feature map, correspond to the spatial dimensions of the image being processed, and may in some cases correspond to a number of pixels/voxels of an image. Depth, as used in reference to a feature map may correspond to a number of features in each feature channel.

The transformations/mappings performed between each feature map are indicated by arrows, wherein each distinct type of arrow corresponds to a distinct type of transformation, as indicated by legend 358. Rightward pointing solid black arrows indicate 3×3 convolutions with a stride of 1, wherein output from a 3×3 grid of features of an immediately preceding feature map (wherein the 3×3 grid extends through all layers of the immediately preceding feature map) are mapped to a single feature, at a single depth, of a current feature map by performing a dot product between the outputs/activations of the 3×3 grid of feature channels and a 3×3 filter, (comprising 9 weights for each layer/unit of depth of the immediately preceding feature map). In some embodiments, the convolutional filter weights may be selected based on noise parameters 204. In some embodiments the convolutional filter weights may be learned during a training process. The filters used to perform the 3×3 convolutions are herein referred to as convolution filters, convolutional filters, convolution kernels, or convolutional kernels.

Downward pointing arrows indicate 2×2 max pooling operations, wherein the max value from a 2×2 grid of feature channels at a single depth is propagated from an immediately preceding feature map to a single feature at a single depth of a current feature map, thereby resulting in an output feature map with a 3-fold reduction in spatial resolution as compared to the immediately preceding feature map. In one example, max pooling of a 2×2 grid of activations from an immediately preceding feature map, wherein the 2×2 grid of activations comprises (2, 1.3, 10, 3.3) produces an output of (10), as 10 is the maximum value of the activations within the 2×2 grid.

Upward pointing arrows indicate 2×2 up-convolutions of stride 2, which comprise performing a transpose convolution (also referred to herein as a deconvolution) using a deconvolution filter comprising a plurality of weights (filters used to perform transpose convolutions are herein also referred to as deconvolutional filters or deconvolution filters) mapping output from a single feature channel at each feature depth of an immediately preceding feature map to a 2×2 grid of features at a single feature depth in a current feature map, thereby increasing the spatial resolution of the immediately preceding feature map 3-fold.

Rightward pointing dash-tailed arrows indicate copying and cropping of a feature map for concatenation with another, later occurring, feature map. Cropping enables the dimensions of the copied feature map to match the dimensions of the feature map with which the copied feature map is to be concatenated. It will be appreciated that when the size of the first feature map being copied and the size of the second feature map to be concatenated with the first feature map, are equal, no cropping may be performed. For example, concatenated feature maps may have the same dimensions, and cropping may not be performed.

Rightward pointing arrows with hollow heads indicate a 1×1 convolution with stride 1, in which each feature channel in an immediately preceding feature map is mapped to a single feature channel of a current feature map, or in other words, wherein a 1-to-1 mapping of feature channels between an immediately preceding feature map and a current feature map occurs. Processing at every feature map may include the above-described convolutions and deconvolutions, as well as activations, where activation functions are non-linear functions that restrict the output values of the processing to a bounded range.

In addition to the operations indicated by the arrows within legend 358, CNN architecture 300 includes solid filled rectangles corresponding to feature maps, wherein feature maps comprise a height (top to bottom length as shown in FIG. 3, corresponds to a y spatial dimension in an x-y plane), width (not shown in FIG. 3, assumed equal in magnitude to height, corresponds to an x spatial dimension in an x-y plane), and depth (a left-right length as shown in FIG. 3, corresponds to the number of features within each feature channel). Likewise, CNN architecture 300 includes hollow (unfilled) rectangles, corresponding to copied and cropped feature maps, wherein copied feature maps comprise height (top to bottom length as shown in FIG. 3, corresponds to a y spatial dimension in an x-y plane), width (not shown in FIG. 3, assumed equal in magnitude to height, corresponds to an x spatial dimension in an x-y plane), and depth (a length from a left side to a right side as shown in FIG. 3, corresponds to the number of features within each feature channel).

Starting at input image tile 302b (herein also referred to as an input layer), data corresponding to a noisy medical image 302a is input and mapped to a first set of features. In some embodiments, noisy medical image 302a comprises one or more layers corresponding to one or more features of the image (such as each intensity value of a multi-color image). In some embodiments, noise parameter layers concatenated with noisy medical image 302a may indicate an expected/anticipated type, or intensity of colored noise at each pixel position of noisy medical image 302a. Noisy medical image 302a may comprise a two-dimensional (2D) or three-dimensional (3D) image/map of a patient anatomical region. In some embodiments, the input data from noisy medical image 302a is pre-processed (e.g., normalized) before being processed by the neural network.

Output layer 356a may comprise an output layer of neurons, wherein each neuron may correspond to a pixel of a predicted de-noised medical image 356b (or residual), wherein output of each neuron may correspond to the predicted pixel intensity in specified location within the output de-noised medical image 356b.

In this way, CNN architecture 300 may enable mapping of a plurality of intensity values from a noisy medical image 302a to a plurality of intensity values of a de-noised medical image 356b, wherein an extent colored noise present in noisy medical image 302a is reduced or eliminated in de-noised medical image 356b. In some embodiments, CNN architecture 300 may enable mapping of one or more features of a pixel/voxel of a noisy medical image to one or more properties de-noised medical image. CNN architecture 300 illustrates the feature map transformations which occur as an input image tile is propagated through the neuron layers of a convolutional neural network, to produce a de-noised medical image. In one example, CNN architecture 300 may enable mapping of a plurality of pixel/voxel intensity values of a noisy medical image to a residual map, wherein a de-noised medical image may be produced by combining the residual map with the input noisy medical image 302a, such as by pixelwise addition of values.

The weights (and biases) of the convolutional layers in CNN architecture 300 may be learned during training, as will be discussed in more detail with reference to FIG. 7 below. CNN architecture 300 may be trained by calculating a difference between a predicted de-noised medical image, and a ground truth de-noised medical image, wherein the ground truth de-noised medical image may comprise a medical image without colored noise. Further, in some embodiments, CNN architecture 300 may select between a plurality of weights learning in training, based on noise parameters 204, in order to select weights calibrated for accurate colored noise reduction with noise parameters 204, for example. When noise parameters 204 are not provided, and only noisy medical image 206 is provided to CNN architecture 300, the CNN architecture may select a set of weights learned in training and calibrated for accurate noise removal for a range of types of colored noise. The difference between the predicted de-noised medical image and the ground truth de-noised medical image may be used to determine a loss, and the loss may be back propagated through the neural network to update the weights (and biases) of each feature map using gradient descent, or any other method of parameter optimization known in the art of machine learning. A plurality of training data pairs, comprising noisy medical images and corresponding ground truth de-noised medical images, may be used during the training process of CNN architecture 300.

Although not shown in FIG. 3, it will be appreciated that the current disclosure encompasses neural network architectures comprising one or more regularization layers, including batch normalization layers, dropout layers, Gaussian noise layers, and other regularization layers known in the art of machine learning which may be used during training to mitigate overfitting and increase training efficiency while reducing training duration.

It should be understood that CNN architecture 300 shown in FIG. 3 is for illustration, not for limitation. Any appropriate neural network can be used herein for predicting a de-noised medical image from a noisy medical image, such as ResNet, recurrent neural networks, General Regression Neural Network (GRNN), etc. One or more specific embodiments of the present disclosure are described above in order to provide a thorough understanding. These described embodiments are only examples of systems and methods for predicting de-noised medical images from noisy medical images using a deep neural network and one or more noise parameters. The skilled artisan will understand that specific details described in the embodiments can be modified when being placed into practice without deviating the spirit of the present disclosure.

Figure 4:
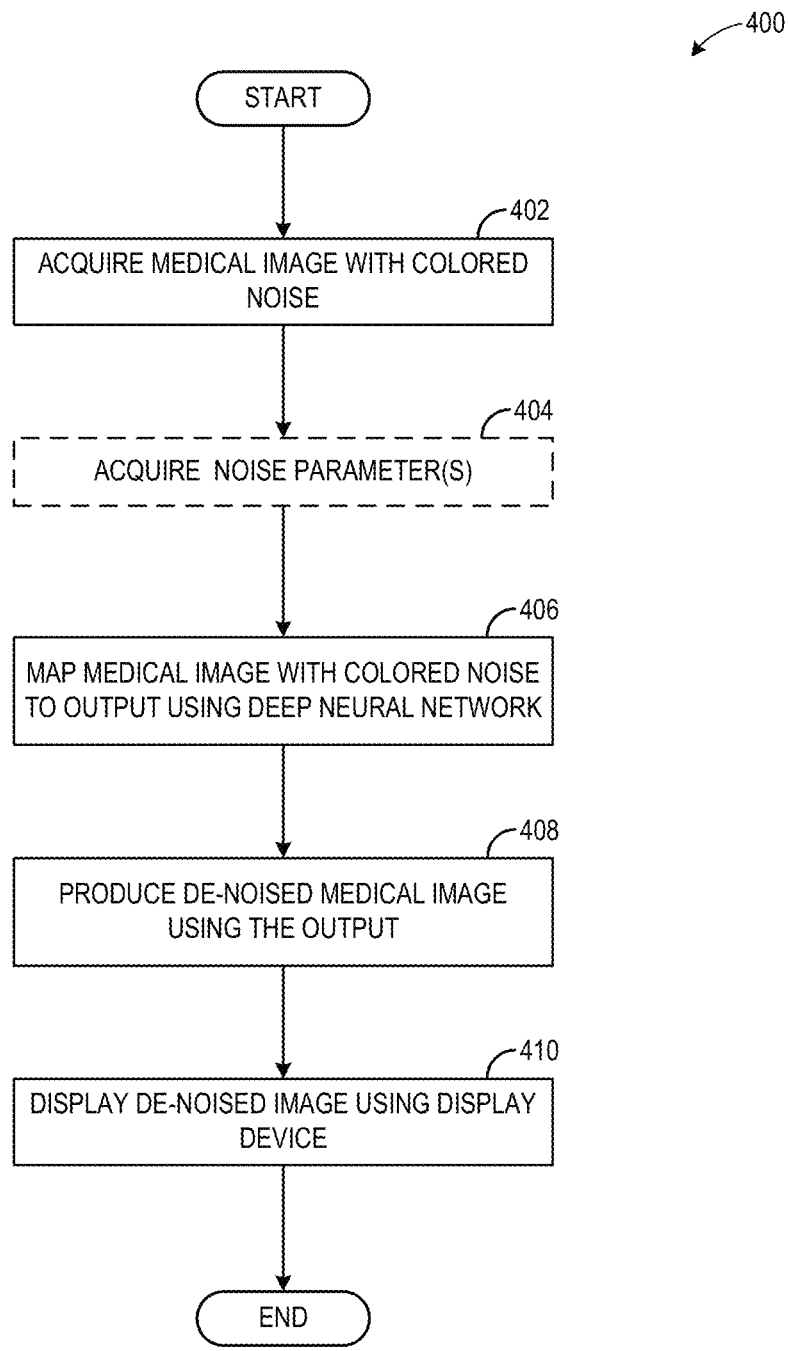
FIG. 4 is a flow chart illustrating a method for removing colored noise from a medical image using a deep neural network, according to an exemplary embodiment.

Referring to FIG. 4, a flow chart of a method 400 for reducing colored noise in a noisy medical image using a deep neural network is shown, according to an exemplary embodiment. Method 400 may be implemented by the image processing system 100, an edge device connected to the imaging device, a cloud in communication with the imaging device, or any appropriate combination thereof. Further, the deep neural network may be the deep neural network 224 shown in FIG. 2, and may have CNN architecture 300 described above in FIG. 3.

Method 400 begins at operation 402, wherein a noisy medical image is acquired. In some embodiments, the image processing system acquires the noisy medical image from an imaging system via communicative coupling, such as over a network. In some embodiments, the image processing system acquires the noisy medical image from non-transitory memory. Although described with reference to a single noisy medical image for simplicity, it will be appreciated that the current disclosure provides for mapping a plurality of noisy medical images to a plurality of (or to a single) de-noised medical image. For example, a number of input layers corresponding to a number of noisy medical images may be increased to accommodate the number of noisy medical images to be de-noised, without deviating from the disclosure herein provided.

At operation 404, method 400 optionally includes acquiring one or more noise parameters associated with the noisy medical image(s). Noise parameters associated with, or corresponding to, a noisy medical image may comprise one or more settings, parameters, or conditions, used or present during acquisition of the noisy medical image. Therefore, in some embodiments, noise parameters comprise settings of an imaging device used during a scan/image acquisition such as a k-space sampling pattern. Noise parameters associated with, or corresponding to, the noisy medical image may comprise one or more parameters regarding the type and distribution of noise in the noisy medical image. Noise parameters may be stored with, or indexed by, the medical image(s) with which they correspond, such that rapid and computationally efficient retrieval of the one or more noise parameters associated with a noisy medical image may be enabled. In particular, the noise parameters may include a k-space sampling pattern used to acquire the medical image, and the k-space sampling pattern may be one of a Parallel Lines with Enhanced Reconstruction (PROPELLER) sampling pattern, a Stack-of-Stars sampling pattern, and a variable density spiral sampling pattern. Additional k-space sampling patterns will be described in more detail in FIG. 7.

At operation 406, the noisy medical image is mapped to an output using the deep neural network. Mapping the noisy medical image to the output comprises inputting data from the noisy medical image, including any additional concatenated data (e.g., noise parameters), into an input layer/input tile of a deep neural network, and propagating the input data through each layer of the deep neural network until an output is produced by an output layer of the deep neural network. In some embodiments, the deep neural network comprises a convolutional neural network, wherein one or more filters (convolutional or deconvolutional) are set based on the noise parameters, and the one or more filters are applied to the data from the noisy medical image as the data propagates through the deep neural network.

Further, when noise parameters are acquired at 404, mapping the noisy medical image to the output at 406 may further comprise incorporating the noise parameters with the deep neural network. In some embodiments, incorporating the noise parameters with the deep neural network comprises concatenating the noise parameter with the noisy medical image and inputting both the noisy image and the blurred medical image into an input layer of the trained deep neural network. In some embodiments, the noise parameters comprises a plurality of values, and incorporating the noise parameters into the deep neural network comprises setting a plurality of weights in the trained deep neural network based on the plurality of values, wherein in some embodiments the deep neural network comprises a CNN, and the plurality of weights comprise a deconvolution filter of a deconvolutional layer or a convolution filter of a convolutional layer of the convolutional neural network. In some embodiments, the noise parameters may be used for both the input layer and the weights of the filters.

At operation 408, a de-noised medical image is generated using the output from the deep neural network. In some embodiments, the output comprises a residual map, and producing the de-noised medical image from the noisy medical image using the output comprises combining the residual map with the noisy medical image to produce the de-noised medical image. In other words, the residual map may comprise a plurality of values, one or each pixel or voxel of the input noisy medical image, which describes the intensity difference between each pixel or voxel of the noisy image and the intensity of each pixel or voxel of a corresponding de-noised medical image. Combining the residual map with the noisy medical image to produce the de-noised medical image may comprise pixelwise addition of values between the residual map and the noisy medical image. In some embodiments, the output from the deep neural network comprises a map of pixel/voxel intensity values of the de-noised medical image.

At operation 410, the image processing system displays the de-noised medical image via a display device. In some embodiments, a user, via a user input device, may select the de-noised image for further image processing, such as image segmentation, pathology identification, super resolution, etc. using models trained on pristine medical images. A difference between the de-noised medical image output by the deep neural network and the corresponding noisy medical image is determined and backpropogated through the layers/feature maps of the deep neural network.

In this way, method 400 enables reduction of colored noise in a noisy medical image in a time-efficient and more consistent manner, via a deep neural network trained on training data with colored noise. Further, by including noise parameters, the deep neural network may more accurately remove colored noise from the noisy medical image by selecting a set of weights calibrated for the noise parameters. Further, the de-noised medical image may be more efficiently processed by further downstream image processing models, which may have been trained using de-noised medical images.

As an example, a method comprises: acquiring a medical image via an imaging system, wherein the medical image comprises colored noise, mapping the medical image to a de-noised medical image using a trained CNN, and displaying the de-noised medical image via a display device. In the previous example, additionally or optionally, mapping the medical image to the de-noised medical image using the trained CNN further includes acquiring one or more noise parameters corresponding to a source of the colored noise, and incorporating the one or more noise parameters into the trained CNN. In one or both of the previous examples, incorporating the one or more noise parameters into the trained CNN includes selecting a set of pre-trained weights and biases of the trained CNN based on the one or more noise parameters, and the one or more noise parameters comprise one or more of a k-space sampling pattern used to acquire the medical image, and a k-space sampling density used to acquire the medical image.

As another example, a method comprises: acquiring a medical image via an imaging system, the medical image comprising colored noise, mapping, by the deep neural network, the noisy medical image to an output, and using the output to generate a de-noised medical image. In the previous example, additionally or optionally, acquiring the noisy medical image further comprises selecting one or more noise parameters, and incorporating the one or more noise parameters into the trained deep neural network. For example, the one or more noise parameters comprise one or more of a k-space sampling pattern used to acquire the medical image and a k-space sampling density used to acquire the medical image, and the medical image is a magnetic resonance (MR) image.

The deep neural network(s) may be trained by using a plurality of pairs of noisy medical images and corresponding pristine images (e.g., image pairs), referred to herein as training data. The noisy image in each image pair is used as input to the deep neural network and the pristine image in each image pair is used as the ground truth for reference. In some examples, an image pair may be produced by applying colored noise to a pristine image, thus generating a corresponding noisy image. Colored noise may be synthesized by weighting a k-space representation of a white-noise image by the noise power derived from a sampling density, and then transforming noise back to the image space. For example, an image space representation of colored noise (e.g., a representation of colored noise in the spatial domain) may be produced by scaling a field of white noise based on a k-space representation of noise power for a k-space sampling pattern, and transforming the resulting noise from the k-space (frequency domain) back to the image space. In this way, a noisy image, with colored noise based on a k-space sampling pattern, may be generated for a pristine image.

Figure 5:
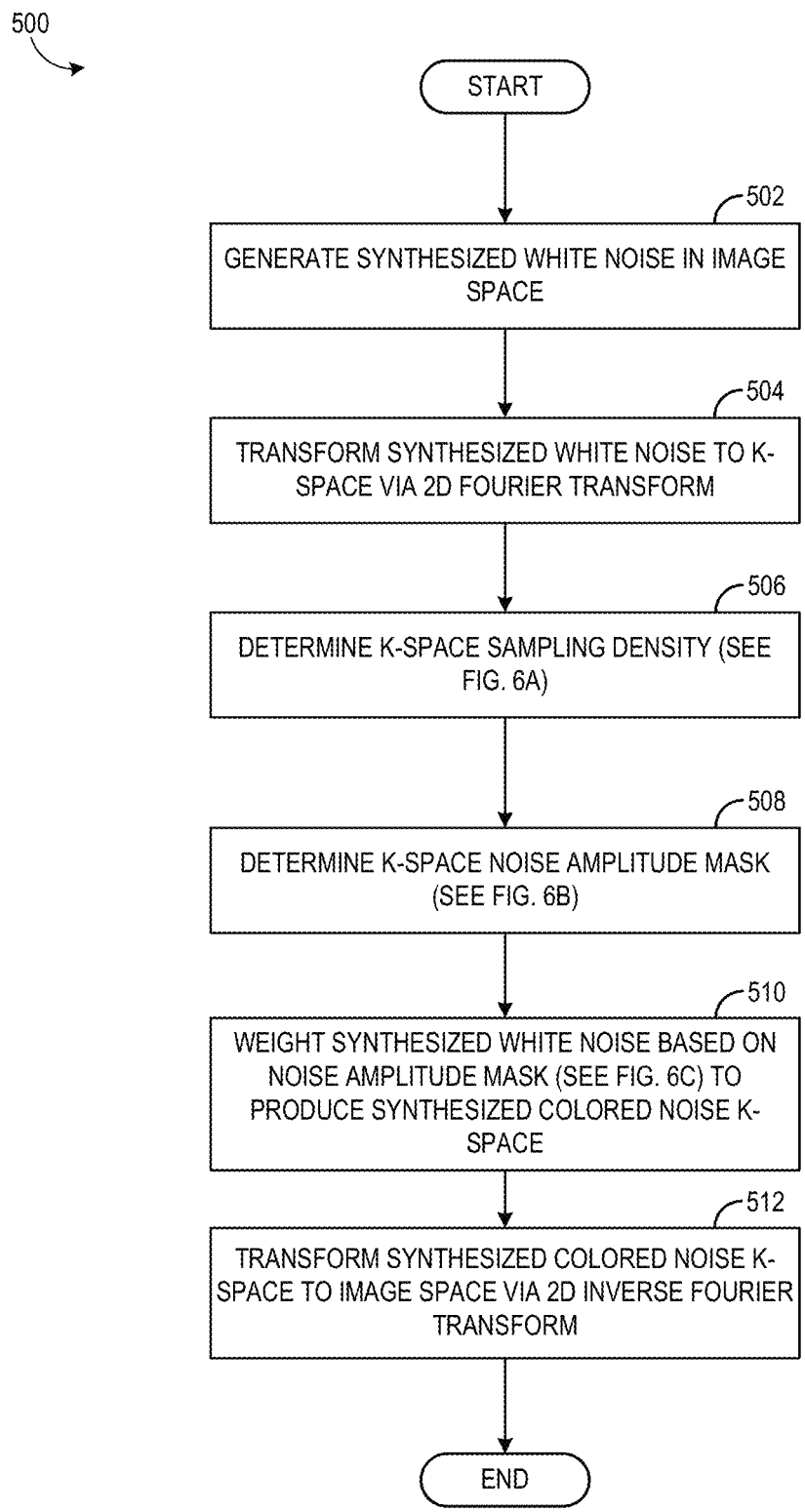
FIG. 5 is a flow chart illustrating a method for synthesizing colored noise based on a noise power for a k-space sampling pattern, according to an exemplary embodiment.

Thus, FIG. 5 shows a flow chart of a method 500 for synthesizing colored noise resulting from nonuniform sampling based on noise power for a k-space sampling pattern. Method 500 may be implemented by the image processing system 100, an edge device connected to the imaging device, a cloud in communication with the imaging device, a computing device in wired communication with the imaging device, or any appropriate combination thereof. Elements of method 500 may be performed sequentially or simultaneously.

At operation 502, method 500 includes synthesizing white noise in image space (e.g., the spatial domain). For example, the synthesized white noise may be a synthesized white noise image, such that noise in the synthesized white noise is equally distributed across all frequencies. In some examples, white noise may be directly synthesized in k-space, rather than in image space.

At operation 504, method 500 includes transforming the synthesized white noise image to k-space (e.g., the frequency domain) via a two-dimensional (2D) Fourier transform. A 2D Fourier transform is a mathematical function which may transform data from a spatial domain (e.g., image space) to a frequency domain (also referred to as k-space). For example, each point in a 2D frequency domain representation of an image corresponds to an amplitude of a sine wave at a certain spatial frequency in the spatial domain representation of the image. A combination of numerical and/or analytical methods may be applied to transform the synthesized white noise image to the k-space via the Fourier transform, and the resulting synthesized white noise k-space may be stored in memory.

Figure 6:
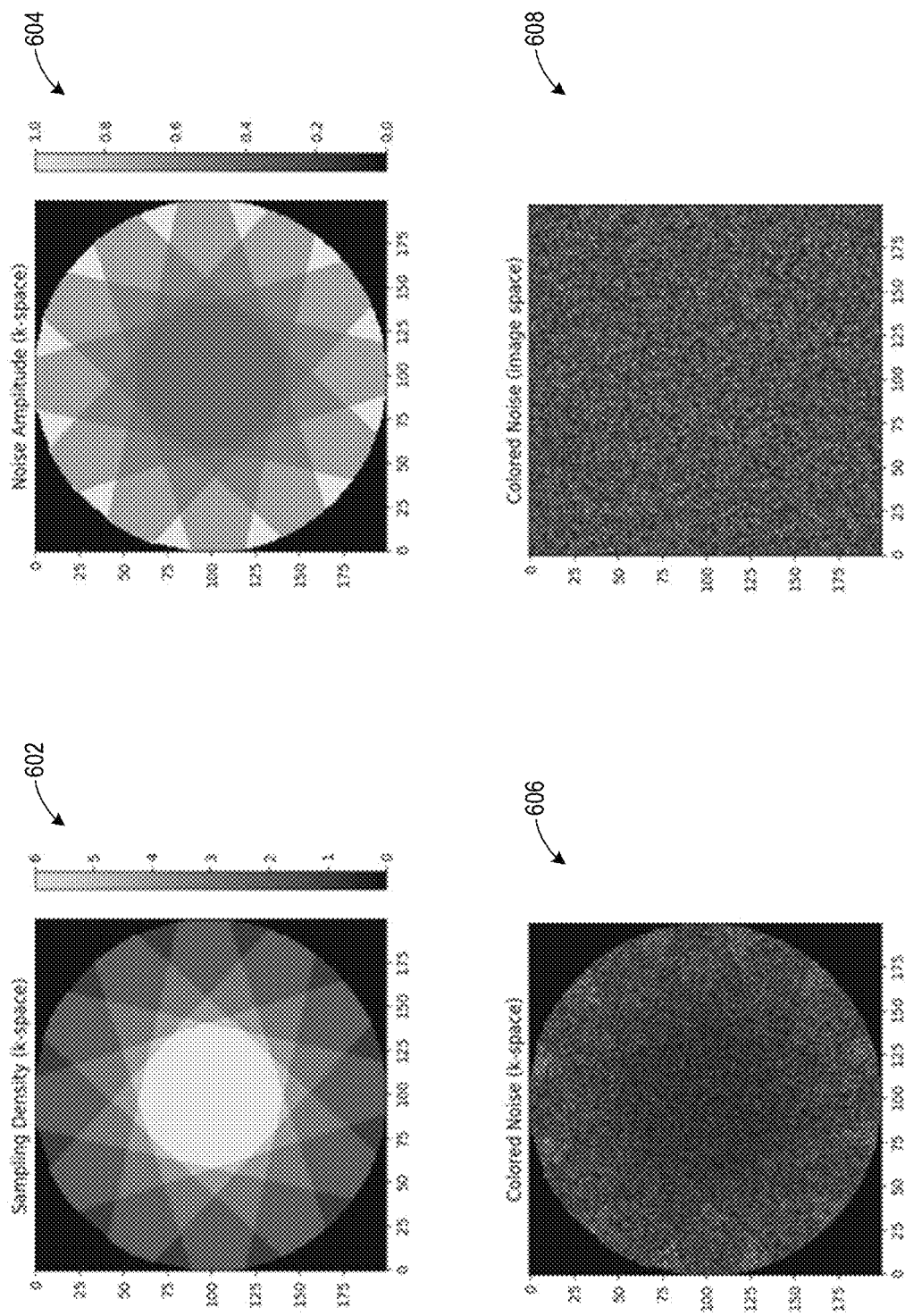
FIG. 6 shows an example of sampling density in the spatial frequency domain, an example of noise power in the spatial frequency domain, an example of synthesized colored noise in the spatial frequency domain, and an example of the synthesized colored noise in the spatial domain, according to an exemplary embodiment.

At operation 506, method 500 includes determining a k-space sampling density. The k-space sampling density may be determined based on a k-space sampling pattern. Any suitable k-space sampling pattern may be used to generate the k-space sampling density, including a Parallel Lines with Enhanced Reconstruction (PROPELLER) sampling pattern, a Stack-of-Stars sampling pattern, a ramp sampling pattern, a weighted average sampling pattern, and a variable density spiral sampling pattern. Turning briefly to FIG. 6, an example k-space sampling density 602 for a k-space sampling pattern is shown. The example k-space sampling density 602 shown in FIG. 6 is the result of a PROPELLER sampling pattern, characterized by multiple intersecting blades, such that central areas have a relatively high k-space sampling density, while outer areas have a relatively low k-space sampling density. For example, the sampling density of a medical image with a PROPELLER sampling pattern may be determined based on blade geometry, blade angle, rotational motion correction, and blade rejection. For a k-space sampling pattern, the k-space sampling density may be determined computationally and/or analytically based on characteristics of the expected sampling pattern.

At operation 508, method 500 includes determining a k-space representation of noise power for the k-space sampling pattern (e.g., a k-space noise power mask), based on the k-space sampling density. Continuing with the example k-space sampling pattern of FIG. 6, the k-space sampling pattern may have a corresponding example k-space noise power mask 604, as shown in FIG. 6. As shown in FIG. 6, example noise power mask 604 may be inversely related to k-space sampling density. For example, a high sampling density in the central region of example k-space sampling density 602 correlates to a low noise power in the central region of example k-space noise power mask 604, as repeated rounds of sampling reduced random noise in the collected data. However, in outer regions of the k-space representation, a low sampling density correlates to a high noise power.

At operation 510, method 500 includes weighting the synthesized white noise k-space based on the example k-space noise power mask to generate a colored noise k-space. Thus, the colored noise k-space (e.g., the k-space representation of synthesized colored noise) may be weighted based on the k-space representation of the example k-space noise power mask, as determined at 508. The output of weighting the synthesized white noise k-space based on the noise power mask is the colored noise k-space. An example colored noise k-space 606 for the sampling pattern is shown in FIG. 6.

At 512, method 500 includes transforming the colored noise k-space to image space via a 2D inverse Fourier transform. The 2D inverse Fourier transform is a mathematical inverse of the 2D Fourier transform used at 504, and may transform a signal from a k-space (e.g., frequency domain) representation to an image space (e.g., spatial domain) representation. For example, a combination of numerical and/or analytical methods may be applied to transform the synthesized colored noise in k-space to the image space via the inverse Fourier transform, and the resulting synthesized colored noise in image space may be stored in memory. An example representation of synthesized colored noise in image space 608 for the expected sampling pattern is shown in FIG. 6.

In this way, colored noise may be synthesized based on a k-space sampling pattern. In other examples, a similar method may be applied to synthesize colored noise based on an image processing method, an image reconstruction method, a noise color, or a noise pattern. Further, in some examples, colored noise may be directly synthesized in k-space based on a noise power map based on a noise parameter. By adding synthesized colored noise to pristine images (e.g., images without noise), corresponding noisy images may be generated. As such an image pair comprises the pristine image and the corresponding noisy image, and the training data for a deep neural net may include a plurality of such image pairs. Further, it should be noted that a variety of k-space sampling patterns may be used to generate colored noise. Accordingly, a plurality of distinct noisy images may be generated from a single pristine image. For example, a first noisy image may include a first pattern of colored noise, while a second noisy image may include a second pattern of colored noise.

As an example, synthesizing colored noise in image space comprises: selecting a k-space sampling pattern, selecting a k-space sampling density, producing a k-space noise power mask based on the k-space sampling pattern and the k-space sampling density, synthesizing a white noise image, taking a two-dimensional Fourier transform of the white noise image to produce a white noise k-space, applying the k-space noise power mask to the white-noise k-space to produce a colored noise k-space, and taking an inverse two-dimensional Fourier transform of the colored noise k-space to produce synthesized colored noise. As another example, for non-Cartesian k-space sampling patterns, a Cartesian representation of the k-space noise may be generated based on a regridding algorithm used to resample the MRI data into a Cartesian coordinate system, rather than weighting a k-space representation of white noise, wherein said regridding algoirhtm comprises one or more regridding algorithms known in the art of image reconstruction.

As another example, synthesizing a colored noise image based on a noise parameter comprises: selecting a k-space sampling pattern based on the noise parameter, selecting a k-space sampling density, producing a k-space amplitude mask based on the k-space sampling pattern and the k-space sampling density, synthesizing a white noise image, generating a white noise k-space based on the white noise image, applying the k-space noise power mask to the white noise k-space to produce a colored noise k-space, generating the colored noise image based on the colored noise k-space, and indexing the k-space sampling pattern to the colored noise image.

Although FIG. 6 shows an example of synthesizing noise based on a PROPELLER sampling pattern, a variety of other k-space sampling patterns may be used without deviating from the scope of the present disclosure. Turning now to FIG. 7, three example k-space sampling patterns are shown. The example k-space sampling patterns shown in FIG. 7 may be used during image acquisition for MR images, and accordingly may be used to synthesize colored noise for training a deep neural network to de-noise images. A first example sampling pattern 702 shows a Cartesian sampling pattern. In first example sampling pattern 702, the k-space sampling pattern comprises a series of parallel lines with a vertical orientation in the k-space representation. Further, as shown, the sampling density is greater in a center portion of the k-space representation, such that a vertical band of higher sampling density spans the k-space representation. In such a k-space sampling pattern as first example sampling pattern 702, noise power may have a first, higher value in the outer portions of the k-space representation, and may have a second, lower value in the center potion due to greater sampling density. A second example sampling pattern 704 shows a radial sampling pattern. In second example sampling pattern 704, sampling is performed in the k-space along radial lines originating in a center of a k-space representation. In such a k-space sampling pattern, a noise power may increase as a function of radius (e.g., distance from the center of the k-space representation), as the sampling density decreases. A third example sampling pattern 706 shows a variable density spiral sampling pattern. In third example sampling pattern 06, sampling is performed in the k-space along a variable density spiral, wherein the sampling is performed along a variable density spiral. In such a k-space sampling pattern, a noise power may increase as a function of the spiral curvature and distance from the center of the spiral, as sampling density decreases. For each expected sampling pattern, sampling density may be determined computationally or analytically.

Figure 7:
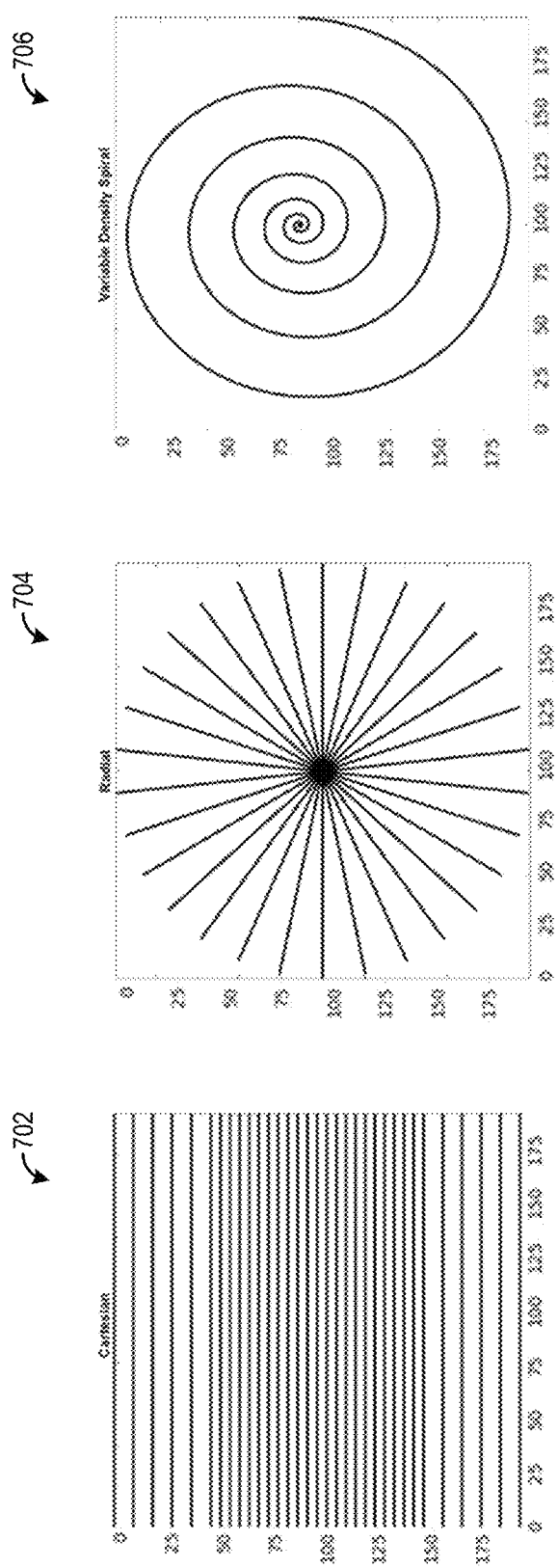
FIG. 7 shows additional example k-space sampling patterns, according to an exemplary embodiment.

Although the k-space sampling patterns shown in FIGS. 6-7 are two-dimensional (2D) k-space sampling patterns, in some embodiments, colored noise may be synthesized for a three-dimensional (3D) sampling method. Specifically, a k-space sampling pattern may be a 3D sampling pattern, but the image denoising may be performed on 2D images resulting from a 3D inverse Fourier transform of 3D k-space data. Note that image noise is stochastic, hence the result of combining independent noise samples can be calculated by adding the square of the noise, the noise power, of the separate samples and then taking the square root. Thus the colored noise in the 2D k-space of the 2D image may be calculated from the 3D k-space noise by calculating the square root of the projection, or line integral, of the noise power through the 3D volume onto the plane of the 2D image. Thus, colored noise may be synthesized for 2D medical images acquired via both 2D k-space sampling patterns and 3D k-space sampling patterns.

Figure 8:
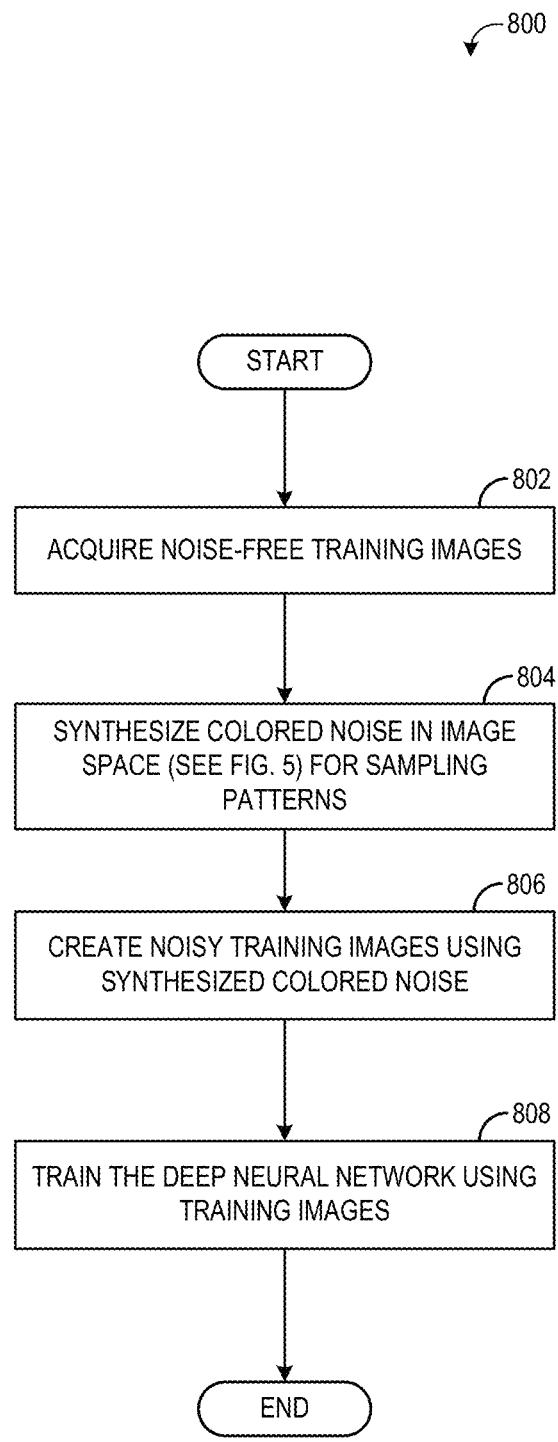
FIG. 8 is a flow chart illustrating a method for generating training data for the deep neural network, according to an exemplary embodiment.

Turning now to FIG. 8, a flowchart of an example method 800 for training a deep neural network (such as CNN 300 shown in FIG. 3) to reduce colored noise in medical images is shown. Method 800 may be executed by one or more of the systems discussed above. In some embodiments, method 800 may be implemented by the system 10 shown in FIG. 1 or the system 200 shown in FIG. 2. In some embodiments, method 800 may be implemented by training module 112, stored in non-transitory memory 106 of image processing system 31.

At operation 802, pristine training images are acquired. For example, the pristine images may be stored in memory, or may be acquired via a wired or wireless connection. The training images may be pristine (e.g., pristine) images, and may include medical images, natural images, synthetic images, and so on. The training images may be selected to efficiently train the neural net to recognize noise in a certain type of medical image, for example.

At operation 804, colored noise is synthesized for a plurality of expected k-space sampling patterns, according to the method of FIG. 5. Synthesizing colored noise for the plurality of expected k-space sampling patterns includes weighting synthesized white noise according to a noise power for each of the plurality of expected k-space sampling patterns. For example, colored noise may be synthesized for each for each of a plurality of expected k-space sampling patterns. Further, additional colored noise may be synthesized to account for other sources of colored noise, such as image post-processing, image reconstruction, etc.

At operation 806, the method includes creating noisy training images using the colored noise synthesized at 804. For example, a noisy image may be generated by applying synthesized colored noise to a pristine image. The noisy image and the corresponding pristine image comprise an image pair. The training data may include a plurality of image pairs, each image pair comprising a pristine image and a noisy image. Further, each image pair in the training data may be indexed to data recording a k-space sampling pattern or other noise parameters used to generate the noisy image. For example, each image pair may be indexed to data recording a k-space sampling pattern used to synthesize colored noise for the noisy image. As another example, each image pair may be indexed to data recording a k-space sampling pattern used to synthesize colored noise for the noisy image. The training data may be stored in memory, for example.

At operation 808, the deep neural network is trained using the training images generated at 806. The deep neural net may be trained using the training images according to any method known in the art. In an embodiment, training the deep neural network includes mapping a noisy image in each image pair in the training data with a corresponding pristine image. For example, for each image pair in the training data, the noisy image is input into an input layer of the deep neural network, along with information regarding a k-space sampling pattern used to generate the noisy image, and mapped to a predicted de-noised image. Further, a difference metric between the predicted de-noised image and the corresponding pristine image (e.g., ground truth image) is calculated by the deep neural network, thus determining an error of the predicted de-noised image relative to the corresponding pristine image. In some embodiments, the difference metric may comprise one or more, or a weighted combination of, a DICE score, a mean square error, an absolute distance error, and an angle error. In some embodiments, training the deep neural network further includes determining a difference between each output from each output neuron of the deep neural network, and a corresponding value in the ground-truth image. Further, the weights and biases of the deep neural network are adjusted based on the difference metric determined between the de-noised image and the pristine image. The difference metric may be back-propagated through the layers of the deep neural network to update the weights (and biases) of the layers. In some embodiments, back-propagation of the loss may occur according to a gradient descent algorithm, or another method of back-propagation known in the art. Further, in some embodiments, a different set of weights and biases may be adjusted based on the synthesized colored noise used to generate the noisy image in the image pair. For example, the deep neural network may include a plurality of sets of weights and biases, each of the plurality of sets of weights and biases corresponding to a particular sampling pattern and/or other noise parameter. In other embodiments, the deep neural network may be trained according to other methods known in the art.

Following operation 808, method 800 may end. It will be noted that 808 may be repeated until the weights and biases of the deep neural network converge, a threshold difference metric is obtained (for the training data or on a separate validation dataset), or the rate of change of the weights and/or biases of the deep neural network for each iteration are under a threshold. In this way, method 800 enables a deep neural network to be trained to identify colored noise in medical images, and to produce de-noised images with substantially less colored noise, thus increasing image resolution and diagnostic quality.

As an example, a method for training a deep neural network to reduce colored noise in medical images comprises: selecting a first medical image devoid of colored noise, synthesizing a colored noise image based on a noise parameter, generating a second medical image by adding the synthesized colored noise to the first medical image, mapping the second medical image to a predicted de-noised medical image via the deep neural network, determining a loss based on a difference between the predicted de-noised image and the first medical image, and updating parameters of the deep neural network based on the loss. In the previous example, additionally or optionally, mapping the second medical image to the predicted de-noised medical image via the deep neural network further includes indexing the noise parameter to the second medical image, and selecting pre-trained weights and biases for the deep neural net based on the noise parameter.

As another example, a medical image is a first medical image, and a method comprises: training a convolutional neural network (CNN) to produce a trained CNN, using a second medical image comprising colored noise and a pristine medical image corresponding to the second medical image, wherein the pristine medical image is devoid of colored noise, and wherein training the CNN comprises: selecting the pristine medical image, synthesizing colored noise in image space, generating the second medical image by adding the synthesized colored noise to the pristine medical image, mapping the second medical image to a predicted de-noised medical image, determining a loss based on a difference between the predicted de-noised medical image and the pristine medical image, and updating parameters of the CNN based on the loss.

Figure 9:
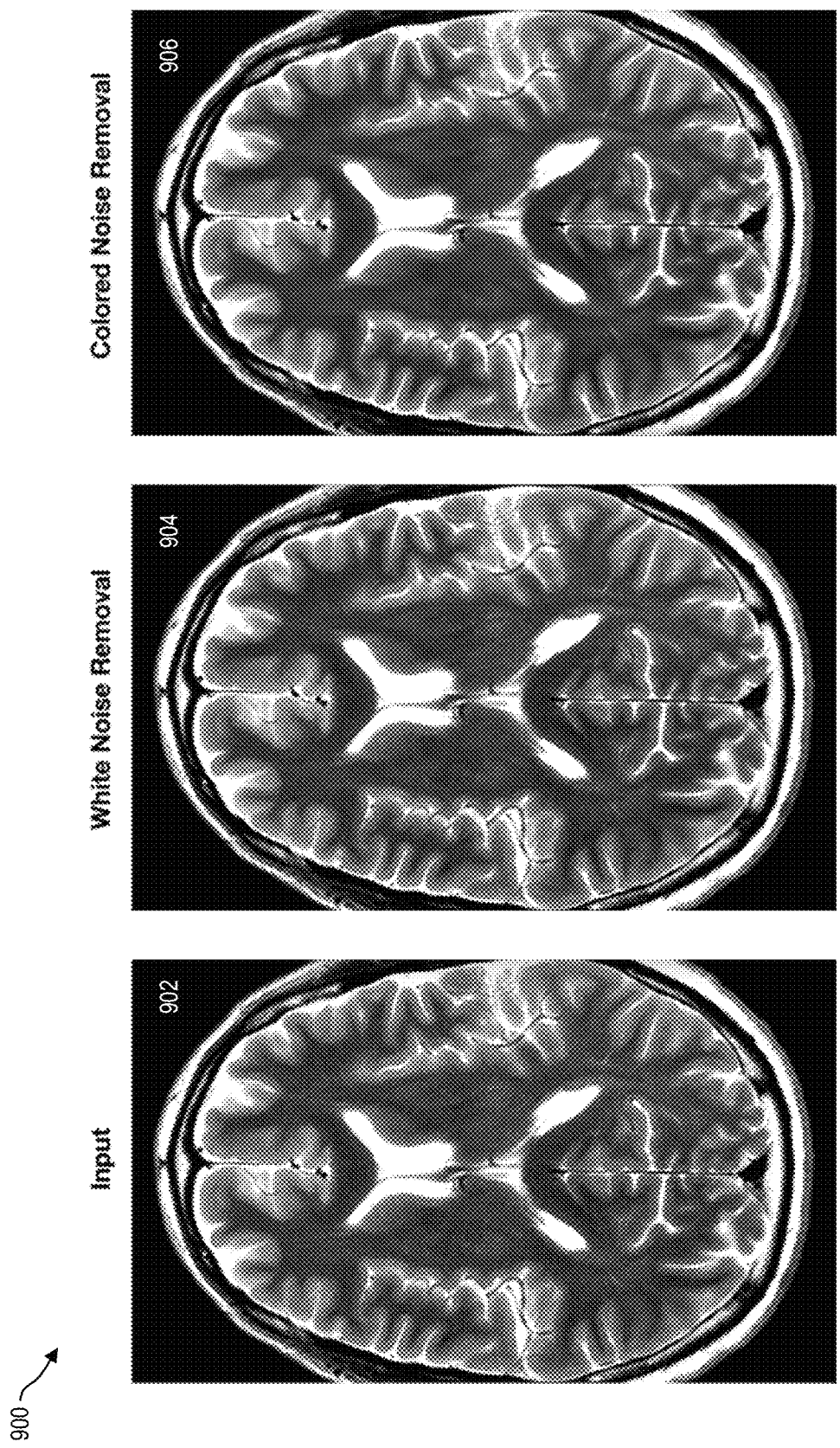
FIG. 9 shows a comparison between a medical image with noise, a medical image after white noise reduction, and a medical image after colored noise reduction, according to an exemplary embodiment.

Turning to FIG. 9, examples are shown of noisy medical images and corresponding de-noised medical images, produced according to embodiments of the present disclosure. In particular, noisy medical image 902 comprises an MR cross-sectional image of a human brain, and includes one or more types of noise which reduce the clarity of the imaged anatomical regions. Noisy medical image 902 may have been produced via a k-space sampling pattern such as the PROPELLER sampling pattern, which includes a non-uniform sampling density and may include colored noise. White noise free medical image 904 comprises the same anatomical regions as depicted in noisy medical image 902, however white pristine medical image 904 is free of white noise, according to existing white noise removal methods (e.g., filtering, deep neural networks, etc.). Although white noise free medical image 904 is less noisy than noisy medical image 902, there remain areas of visible noise in white noise free medical image 904. In contrast, colored noise free medical image 906 comprises the same anatomical regions as depicted in noisy medical image 902 and white noise free medical image 904, but is free of colored noise, according to the colored noise reduction method herein disclosed, such as method 400. As can be seen, the colored noise free medical image 906 is sharper and less noisy than either of noisy medical image 902 and white noise free medical image 904, which may enable more precise analysis and/or diagnosis based on the imaged anatomical regions. For example, after colored noise reduction, the medical image may be viewed at a higher resolution, or may be used for more detailed analysis of a condition of a patient.

Figure 10:
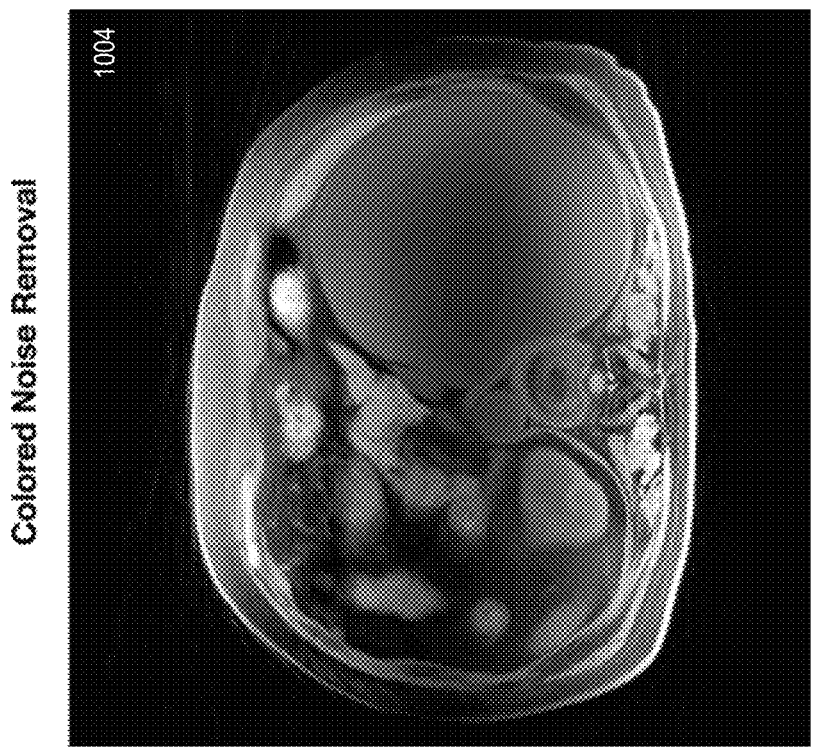
FIG. 10 shows a comparison between a medical image with noise, and a medical image after colored noise reduction, according to an exemplary embodiment.
Figure 10:
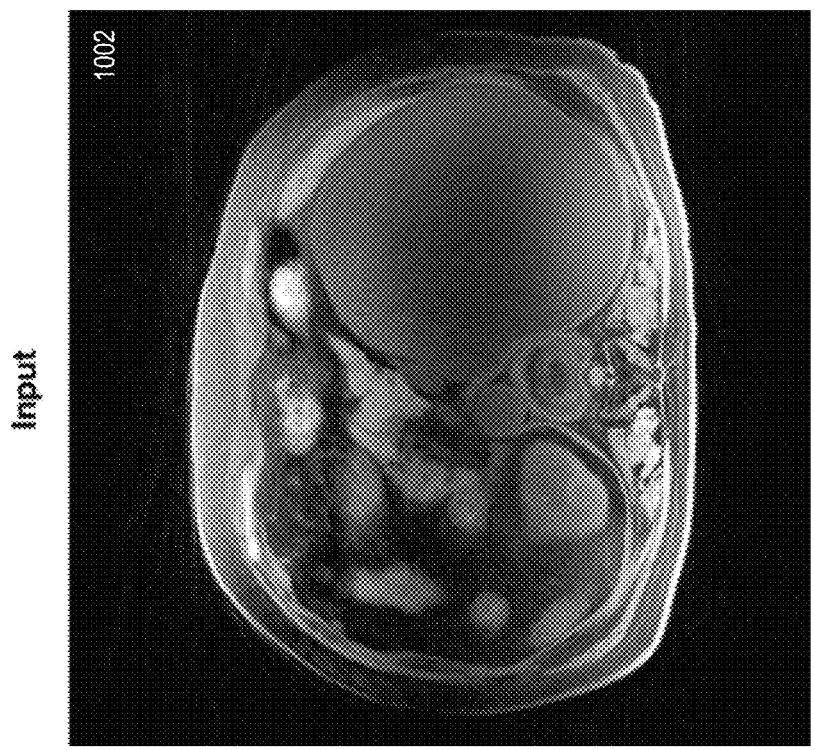

Next, in FIG. 10, further examples are shown of noisy medical images and corresponding de-noised medical images, produced according to embodiments of the present disclosure. In particular, noisy medical image 1002 comprises an MR cross-sectional image of a human abdomen, and includes one or more types of noise which reduce the clarity of the imaged anatomical regions. Noisy medical image 1002 may have been produced via a k-space sampling pattern such as a Stack of Stars sampling pattern, which includes uneven sampling and may produce colored noise. In contrast, noise free medical image 1004 comprises the same anatomical regions as depicted in noisy medical image 902, but is free of colored noise, according to the colored noise reduction method herein disclosed, such as method 400. As can be seen, the colored noise free medical image 1004 is sharper and less noisy than noisy medical image 1002 and white noise free medical image 904, which may enable more precise analysis and/or diagnosis based on the imaged anatomical regions.

Although FIGS. 9 and 10 provide two specific examples of anatomical regions, imaged via MRI, which may be de-noised using the systems and methods disclosed herein, it will be appreciated that the current disclosure provides for de-noising of substantially any medical images of any anatomical region. In one embodiment, a single deep neural network may be trained using training data pairs of substantially similar anatomical regions, captured/acquired using a single medical imaging modality, and the deep neural network may be employed in de-noising of noisy medical images of anatomical regions substantially similar to those of the training data pairs. In other embodiments, a single deep neural network may be trained using training data pairs comprising a plurality of distinct medical imaging modalities of distinct anatomical regions, thereby producing a more generalized deep neural network which may enable de-noising of a wide range of medical images of various anatomical regions using a single deep neural network. In this way, colored noise may be substantially reduced in medical images via a deep neural network, increasing image resolution.

The technical effect of training a deep neural network to de-noise images with synthesized colored noise based on a k-space sampling pattern is that the deep neural network may be enabled to accurately reduce colored noise in medical images with a wide range of types of colored noise.

One or more specific embodiments of the present disclosure are described above in order to provide a thorough understanding. These described embodiments are only examples of systems and methods for selectively de-noising a medical image by using a deep neural network. The skilled artisan will understand that specific details described in the embodiments can be modified when being placed into practice without deviating the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method comprising:
    receiving a medical image acquired by an imaging system, wherein the medical image comprises colored noise;
    mapping the medical image to a de-noised medical image without colored noise using a trained convolutional neural network (CNN);
    displaying the de-noised medical image via a display device;
    wherein mapping the medical image to the de-noised medical image using the trained CNN further includes:
        acquiring one or more noise parameters corresponding to a source of the colored noise and incorporating the one or more noise parameters into the trained CNN; and
    wherein the one or more noise parameters are derived from at least one of a k-space sampling pattern used to acquire the medical image or a k-space sampling density used to acquire the medical image.

2. The method of claim 1, wherein incorporating the one or more noise parameters into the trained CNN includes selecting a set of pre-trained weights and biases of the trained CNN based on the one or more noise parameters.

3. The method of claim 1, wherein the k-space sampling pattern is one of a Parallel Lines with Enhanced Reconstruction (PROPELLER) sampling pattern, a Stack-of-Stars sampling pattern, a ramp sampling pattern, a weighted average sampling pattern, and a variable density spiral sampling pattern.

4. The method of claim 1, wherein the method further comprises:
    training a CNN to produce the trained CNN, using a training medical image comprising colored noise and a pristine medical image corresponding to the training medical image, wherein the pristine medical image is devoid of colored noise, and wherein training the CNN comprises:
        selecting the pristine medical image;
        synthesizing colored noise in image space;
        generating the training medical image by adding the synthesized colored noise to the pristine medical image;
        mapping the training medical image to a predicted de-noised medical image;
        determining a loss based on a difference between the predicted de-noised medical image and the pristine medical image; and
        updating parameters of the CNN based on the loss.

5. The method of claim 4, wherein synthesizing colored noise in image space comprises:
    selecting a k-space sampling pattern;
    selecting a k-space sampling density;
    producing a k-space noise power mask based on one or more of the k-space sampling pattern, a regridding algorithm, and the k-space sampling density;
    synthesizing a white noise image;
    taking a Fourier transform of the white noise image to produce a white-noise k-space;
    applying the k-space noise power mask to the white-noise k-space to produce a colored noise k-space; and
    taking an inverse Fourier transform of the colored noise k-space to produce synthesized colored noise.

6. The method of claim 5, wherein mapping the training medical image to the predicted de-noised medical image comprises:
    indexing the k-space sampling pattern to the training medical image; and
    selecting a set of weights and biases of the CNN based on the k-space sampling pattern.

7. A method for training a deep neural network to reduce colored noise in medical images comprising:
    selecting a first medical image devoid of colored noise;
    synthesizing a colored noise image based on a noise parameter;
    generating a second medical image by adding the synthesized colored noise image to the first medical image;
    mapping the second medical image to a predicted de-noised medical image via the deep neural network;
    determining a loss based on a difference between the predicted de-noised medical image and the first medical image;
    updating parameters of the deep neural network based on the loss; and
    wherein synthesizing the colored noise image based on the noise parameter further comprises:
        selecting a k-space sampling pattern based on the noise parameter;
        selecting a k-space sampling density;
        producing a k-space noise power mask based on at least one of the k-space sampling pattern, a regridding algorithm, or the k-space sampling density;
        synthesizing a white noise image;
        generating a white-noise k-space based on the white noise image;
        applying the k-space noise power mask to the white-noise k-space to produce a colored noise k-space;
        generating the colored noise image based on the colored noise k-space; and
        indexing the k-space sampling pattern to the colored noise image.

8. The method of claim 7, wherein mapping the second medical image to the predicted de-noised medical image via the deep neural network further includes:
    indexing the noise parameter to the second medical image; and
    selecting a set of weights and biases for the deep neural network based on the noise parameter.

9. The method of claim 7 further comprising:
    receiving a medical image acquired using an imaging system, the medical image comprising colored noise;
    mapping, by the deep neural network, the medical image to an output; and
    using the output to generate a de-noised medical image.

10. The method of claim 9 wherein receiving the medical image further comprises:
    selecting one or more noise parameters; and
    incorporating the one or more noise parameters into the trained deep neural network.

11. The method of claim 10, wherein the one or more noise parameters comprise one or more of a k-space sampling pattern used to acquire the medical image and a k-space sampling density used to acquire the medical image.

12. The method of claim 7, wherein the k-space sampling pattern is a 3D (three-dimensional) k-space sampling pattern, and the k-space noise power mask is a two-dimensional (2D) projection of a 3D noise power in k-space.

13. A system comprising:
a memory storing a deep neural network;
a display device; and
a processor communicably coupled to the memory and configured to:
receive a medical image acquired using a magnetic resonance imaging (MRI) system, wherein the medical image comprises colored noise;
map the medical image to a de-noised medical image using a trained deep neural network; and
display the de-noised medical image via the display device,
wherein mapping the medical image to the de-noised medical image using the trained deep neural network further includes:
acquiring one or more noise parameters corresponding to a source of the colored noise and incorporating the one or more noise parameters into the trained deep neural network, and
wherein the one or more noise parameters are derived from at least one of a k-space sampling pattern used to acquire the medical image or a k-space sampling density used to acquire the medical image.

14. The system of claim 13, wherein the processor is further configured to:
receive one or more noise parameters associated with the colored noise; and
incorporate the one or more noise parameters into the trained deep neural network.

15. The system of claim 13, wherein the medical image is a first medical image, and wherein the processor is further configured to train a deep neural network using a pristine medical image and a second medical image with colored noise to produce the trained deep neural network.

16. The system of claim 15, wherein the processor is configured to train the deep neural network using the pristine medical image and the second medical image with colored noise by:
selecting the pristine medical image from a plurality of pristine medical images;
synthesizing colored noise in image space;
adding the synthesized colored noise to the pristine medical image to produce the second medical image comprising the synthesized colored noise;
mapping the second medical image to a predicted de-noised medical image;
determining a loss based on a difference between the predicted de-noised medical image and the pristine image; and
updating parameters of the deep neural network based on the loss.

* * * * *